United States Patent [19]

Vilcek et al.

[11] Patent Number: 4,460,685
[45] Date of Patent: Jul. 17, 1984

[54] METHOD OF ENHANCING THE PRODUCTION OF HUMAN γ INTERFERON

[75] Inventors: Jan T. Vilcek, New York; Yum K. Yip, Forest Hills, both of N.Y.

[73] Assignee: New York University, New York, N.Y.

[21] Appl. No.: 255,257

[22] Filed: Apr. 17, 1981

Related U.S. Application Data

[63] Continuation-in-part of Ser. No. 154,310, May 29, 1980, abandoned.

[51] Int. Cl.³ .................. C12P 21/02; C12P 19/34; C12N 15/00; C12N 1/38
[52] U.S. Cl. .................................... 435/70; 435/91; 435/172.3; 435/811; 435/244; 935/34; 424/85
[58] Field of Search .............. 435/68, 70, 172, 811, 435/91, 244

[56] References Cited

U.S. PATENT DOCUMENTS 4,262,090 4/1981 Colby et al. ............... 435/172

OTHER PUBLICATIONS

Stringfellow, Interferon and Interferon Inducers, Marcel Dekker, Inc., pp. 3–7 and 145–151 (1980).
Dianzani et al., Infection and Immunity, pp. 879–882 (Dec. 1979).
Research Disclosure No. 18309, Jul. 1979.
Vilcek et al., Cell Substrate, pp. 117–127, Plenum Pub. Corp. (1979).
Vilcek et al., Microbiology 1980 pp. 204–207, American Society for Microbiology (1980).
Vilcek et al., Biochemical Characterization of Lymphokines, pp. 323–329, Academic Press (3–1980).
Klein et al., J. Gen. Virol., pp. 111–117, vol. 46 (1980).
Langford et al., Infection and Immunity, pp. 62–68 (Oct. 1978).
Vilcek et al., Abstract No. 59, 2nd International Workshop, Wolfsberg/Ermatingen/Switzerland (5–1979).
Langford et al., Infection and Immunity, pp. 36–41 (Oct. 1979).
Program, Biochemical Characterization of Lymphokines, 2nd International Lymphokine Workshop, Switzerland (5–1979).

*Primary Examiner*—Alvin E. Tanenholtz
*Attorney, Agent, or Firm*—Hamilton, Brook, Smith & Reynolds

[57] ABSTRACT

A method for stimulating the production of human IFN-γ in a culture of cells is disclosed. In this method, an effective amount of a diterpene compound is added to a culture of IFN-γ producing cells.

32 Claims, No Drawings

METHOD OF ENHANCING THE PRODUCTION OF HUMAN γ INTERFERON

GOVERNMENT SUPPORT

Work described herein, and in parent application Ser. No. 154,310, has been partially supported by grants and contracts from the U.S. Department of Health and Human Services (HHS) or its predecessor organizations.

RELATED APPLICATION

This is a continuation-in-part of U.S. Ser. No. 154,310, filed May 29, 1980 and now abandoned.

TECHNICAL FIELDS

This invention is in the fields of cell biology and immunology.

BACKGROUND ART

Interferon is a potent antiviral glycoprotein released by animal cells following viral infection and also after treatment of such cells with certain nonviral inducers. It constitutes one of the major defense mechanisms against viral infections in mammals, including humans. In addition to its antiviral function, interferon has been found to have immunoregulatory activities, to affect various cellular functions including cell division, and to have value as an anticancer drug.

Much research and development effort has been applied to the large scale production of human interferon. During the course of these efforts, it was learned that there are at least three distinct species of human interferon. "α" or "Le" interferon is the major interferon species produced in cells of lymphoid origin, whereas "β" or "F" interferon is the predominant species obtained after induction of non-lymphoid cells. In addition, there is a third interferon species, which has variously been referred to as "γ", "immune" or "type II" interferon, that is preferentially produced in cultures of lymphocytes, particularly in cultures enriched for T cells. Although it is not certain that T lymphocytes are the only source of this interferon species, it has also been suggested that this species be referred to as "T-type" interferon. See Wietzerbin, J. et al., "Immune Interferon Induced by Phytohemagglutinin in Nude Mouse Spleen Cells", Infect. Immun. 21, 966–72 (1978). In view of this, the terms "γ-type interferon," "γinterferon" or simply IFN-γ will be used throughout this description, and are meant to include "immune," "Type II" or "T-type" interferon.

Each of the three species of interferon fit the general definition for interferon in that they are induced proteins that, on incubation with competent cells, produce a characteristic antiviral state. Nevertheless, these three interferon species have distinct properties including their antigenic characteristics and their physicochemical properties. See Vilcek, J. et al., "Synthesis and Properties of Various Human Interferons," Microbiology-1980, Amer. Soc. for Microbiology, Washington, D.C., pp. 204–207 (1980).

IFN-γ is produced by lymphocytes in response to mitogens, or by sensitized T lymphocytes in response to specific antigens. A characteristic property of IFN-γ is its lack of stability at pH 2. This property is often used as the major criterion for distinguishing IFN-γ from other species. An additional distinguishing property is based upon immunological analysis even though antiserum against human IFN-γ is not yet available. Antisera to α and β interferon are available and they neither neutralize nor bind IFN-γ. Thus, IFN-γ is presently defined as being antigenically "non-α, non-β".

Although it has been suspected that IFN-γ might be more efficient in its immunoregulatory, cell growth inhibitory and tumor growth inhibitory activities than other interferon species, very little definitive information has been available about IFN-γ because good production and purification methods have not been discovered.

One of the most widely employed methods for producing human IFN-γ to data has been the induction of human lymphocyte cells in cell culture with the plant lectin, phytohemagglutinin. See Wheelock, E. F., "Interferon-Like Virus Inhibitor Induced in Human Leukocytes by Phytohemagglutinin," Science 149, 310-11 (1965). Although widely used, the production with phytohemagglutinin-induced lymphocyte cells has invariably produced relatively low yields of IFN-γ.

DISCLOSURE OF THE INVENTION

This invention relates to the production of IFN-γ and is based upon the discovery that the addition of certain diterpene compounds to cultures of white blood cells (leukocytes) can provide significant stimulation of human IFN-γ production. Stimulation of IFN-γ production has been achieved with and without the addition of a known inducer, such as phytohemagglutinin. In preferred embodiments, a diterpene compound and IFN-γ inducer are added to cultures of white blood cells to achieve the desired stimulation of IFN-γ production.

The addition of a diterpene compound to stimulate IFN-γ production increases the level of mRNA for IFN-γ present in the cultures. This increased level of mRNA for IFN-γ facilitates the isolation of such mRNA, which can then be employed in subsequent creation and cloning of a recombinant DNA molecule containing the genetic sequence for IFN-γ.

Thus, this invention provides a method for stimulating IFN-γ production thereby increasing the likelihood that significant quantities can be produced under commercially practical conditions. The invention further provides a method for increasing the production in cell cultures of mRNA for IFN-γ which is useful in the isolation of this mRNA so that it can be employed in production of IFN-γ by recombinant DNA procedures or other biological procedures requiring isolated mRNA.

BEST MODE OF CARRYING OUT THE INVENTION

Initially, a culture of cells capable of elaborating human IFN-γ in a cell culture medium is formed. Such cells are typically sensitized lymphocytes, which can be induced by specific antigens, or unsensitized lymphocytes, which can be induced by mitogens. Of course, any other cell type capable of elaborating human IFN-γ would be suitable for use with this invention.

In practice, the white blood cell cut (leukocytes) can be employed. This cut can be obtained from the buffy coat of a unit of blood or by cytopheresis. For example, a purified lymphocyte fraction can be employed, which can be obtained by blood centrifugation, column adsorption, or other art-recognized techniques. Nevertheless, in some experiments described subsequently, unprocessed platelet pheresis residues or unprocessed buffy coat layers were more efficient interferon producers than their purified counterparts. The ability to omit a cell cut purification step simplifies the overall methodology, and appears to have the additional benefit of more efficient IFN-γ production in such cases.

Cell culture media are employed in culturing the cells. Generally, these are synthetic formulations designed to provide sources of amino acids, vitamins, glucose, etc., to the growing cells. Typical culture media include RPMI 1640 medium, Eagle's medium, the Dulbecco-Vogt modification of Eagle's medium, and Ham's medium. Serum supplement may be added to the medium to provide certain proteins, and suitable examples of serum supplements include human plasma proteins, calf serum and fetal calf serum.

Some cells suitable for producing IFN-γ can be grown in suspension cultures, such as various lymphoid lines. If, however, the cells attach to a solid surface, culture dishes, prescription bottles, roller tubes, roller bottles, roller bottles, multi-tray units, or microcarriers can be employed.

In general, art-recognized techniques are employed to culture the white blood cells. Thus, those skilled in the art will recognize, or be able to ascertain using routine experimentation, many equivalents to the methods for obtaining and culturing cells which have been specifically mentioned above.

Human IFN-γ can be induced in these cultures by adding an inducer for this interferon species. Mitogens, including plant lectins such as phytohemagglutinin (PHA) and concanavalin A (CON A), are known interferon inducers. See Friedman, R. and Cooper, H., "Induction of Interferon in Lymphocytes by Mitogens," *Proc. Soc. Exptl. Biol. Med.* 125, 901–5 (1967) and Wheelock, E. F. (1965), cited above. In addition, certain bacterial toxins, such as staphylococcal enterotoxin A have more recently been found to induce human IFN-γ from lymphocyte cells. See Langford, M. P. et al., "Large-Scale Production and Physicochemical Characterization of Human Interferon," *Infect. Immun.* 26, No. 1, 36–41 (1979). Additionally, recent work indicates that certain enzymes, such as galactose oxidase, also induce human IFN-γ production from lymphocytes. See Dianzani, F. et al., "Enzymatic Induction of Interferon Production by Galactose Oxidase Treatment of Human Lymphoid Cells," *Infect. Immun.* 26, No. 3, 879–82 (1979). It is also known that human IFN-γ can be induced in cultures of lymphocytes from sensitized donors by specific antigens, such as tuberculin. See Vilcek, J. et al., "Synthesis and Properties of Various Human Interferons," Microbiology-1980, Amer. Soc. for Microbiology, Washington, D.C., pp. 204-7 (1980). Protein A is another recognized IFN-γ inducer. See Ratliff, L. R., McCool, R. E. and Catalona, W. S., "Interferon Induction and Augmentation of Natural-Killer Activity by Staphylococcus Protein A," *Cell. Immun.* 57, 1–12 (1981). Still yet another inducer is antilymphocyte serum, including monoclonal antibodies. See Falcoff, E. et al., "Synthesis of Interferon in Human Lymphocytes Stimulated in vitro by Antilymphocytic Serum," *Eur. J. Clin. Biol. Res.* 17, 20–6 (1972). Other inducers of human IFN-γ are, of course, suitable for use with the techniques of this invention.

Although such known IFN-γ inducers are usually employed in addition to a diterpene compound, this is not always necessary or desirable. As will be apparent from the experimental results presented subsequently, a significant stimulation of IFN-γ production can sometimes be achieved without the presence of a separate inducer. Thus, where a known inducer other than the diterpene compound is employed, the diterpene compound can be considered to "enhance" IFN-γ interferon production. Where the diterpene compound is used alone, it might itself be considered as an "inducer" of IFN-γ. In both cases, the diterpene compound can be considered to "stimulate" IFN-γ production.

In the production of interferons, priming the cultures with relatively small amounts of interferon, as well as superinduction techniques, have often been shown to increase production. It is believed that such priming and superinduction techniques may also be beneficially employed with the enhanced production of IFN-γ described herein.

The agents found to stimulate human IFN-γ production are certain diterpene compounds, referred to herein as "γ interferon production stimulating" diterpene compounds. Diterpene compounds, particularly esters, have been isolated from plant products, such as croton oil, and the diterpene moiety is derived from the tetracyclic hydrocarbon tigliane. See Hecker, E., "Structure Activity Relationships in Diterpene Esters Irritant and Cocarcinogenic to Mouse Skin," *Carcinogenesis* 2, Mechanisms of Tumor Promotion and Carcinogenesis, ed. Slaga, T. J., Sivak, A. and Boutwell, R. K., Raven Press, N.Y. (1978), the teachings of which are hereby incorporated by reference.

One class of suitable diterpene compounds is known as phorbol esters, which have structural formulas represented by:

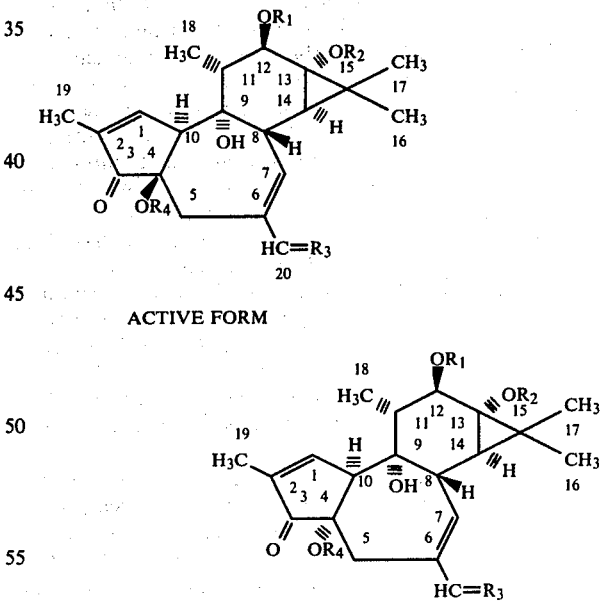

ACTIVE FORM

INACTIVE 4-alpha ISOMER wherein $R_1$, $R_2$, $R_3$ and $R_4$ are individually selected from hydrogen, alkyl, alkoxy, carboxy, keto, aryl and alkaryl groups, and at least one of $R_1$ and $R_2$ forms as ester functionality at the 12 or 13 ring position. $R_1$ and/or $R_2$ are derived from carboxylic acids to form the ester bonds, and these carboxylic acids can be saturated or unsaturated hydrocarbons and also may include residues of cyclic compounds (e.g., benzene) in their chain.

See, for example, Kupchan, S. M., Sweeney, J. G., Baxter, R. L., Tatsuki, M., Zimmerly V. A. and Sickles, B. R., *J. Am. Chem. Soc.* 97:3 (1975).

Some specific examples of phorbol ester compounds and their abbreviations are illustrated in Table I, which follows.

TABLE I

| Name | Abbrev. | $R_1$ | $R_2$ | $R_3$ | $R_4$ |
|---|---|---|---|---|---|
| Phorbol | (PHR) | H | H | H, OH | H |
| Phorbol 12,13-diacetate | (PDA) | $CH_3CO-$ | $CH_3CO-$ | H, OH | H |
| Phorbol 13,20-diacetate | (P13,20DA) | H | $CH_3CO-$ | $CH_3CO-$ | H |
| Phorbol 12, 13-dibenzoate | (PDBz) | $C_6H_5CO-$ | $C_6H_5CO-$ | H, OH | H |
| Phorbol 12,13-dibutyrate | (PDB) | $C_3H_7CO-$ | $C_3H_7CO-$ | H, OH | H |
| Phorbol 12,13-didecanoate | (PDD) | $C_9H_{19}CO-$ | $C_9H_{19}CO-$ | H, OH | H |
| Phorbol (4-O—methyl) 12-myristate-13-acetate | (MPMA) | $C_{13}H_{27}CO-$ | $CH_3CO-$ | H, OH | $CH_3-$ |
| Phorbol 12-monomyristate | (PM) | $C_{13}H_{27}CO-$ | H | H, OH | H |
| Phorbol 12-myristate-13-acetate | (PMA or TPA) | $C_{13}H_{27}CO-$ | $CH_3CO-$ | H, OH | H |
| Phorbol (20-oxo-20-deoxy) 12-myristate-13 acetate | (PMAAL) | $C_{13}H_{27}CO-$ | $CH_3CO-$ | =O | H |
| 4 alpha-Phorbol | (4 -PHR) | H | H | H, OH | H |
| 4 alpha-Phorbol 12,13-didecanoate | (4 -PDD) | $C_9H_{19}CO-$ | $C_9H_{19}CO-$ | H, OH | H |

Some of these phorbol ester compounds have been shown to be tumor-promoting. See Van Duuren, B. L., "Tumor-Promoting and Co-Carcinogenic Agents in Chemical Carcinogenesis," *Chemical Carcinogens,* ACS Monograph 173, Ed. Searle, C. E. (1976). At least one of these tumor-promoting phorbol ester compounds, phorbol 12-myristate-13-acetate (PMA), also sometimes named 12-0-tetradecanoylphorbol-13-acetate (TPA), has been found particularly effective for stimulating IFN-γ production from induced white blood cells. Thus, TPA is a preferred phorbol ester for purposes of stimulating IFN-γ production.

Another plant-derived diterpene ester, mezerein, has been found to be an effective agent for stimulating IFN-γ production. Mezerein has been found to elicit many of the same cellular responses as TPA, but is much less effective as a tumor promoter, and in fact has significant antileukemic activity. See Mufson, R. A. et al., "Effects of 12-0-Tetradecanoylphorbol-13-acetate and Mezerein on Epidermal Ornithine Decarboxylase Activity, Isoproteronol-stimulated Levels of Cyclic Adenosine 3':5'-Monophosphate, and Induction of Mouse Skin Tumors in Vivo," *Can. Res.* 39, 4791-5 (1979). It has a structural formula closely related to phorbol esters, as can be seen from the following structural formula for mezerein, which is taken from Kupchan, S. M. and Baxter, R. L., "Mezerein: Antileukemic Principle Isolated from Daphne mezereum L," *Science* 187, 652 (1974):

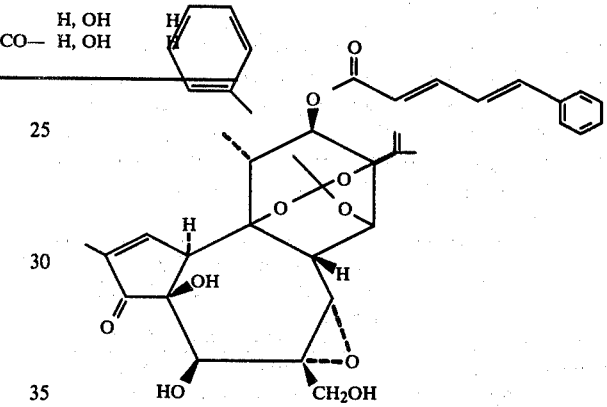

Although TPA was added prior to the inducer in many of the experiments described below, the diterpene compound can also be added at approximately the same time as inducer is added, and possibly subsequently. In fact, as described herein, a separate inducer may be entirely omitted in some cases.

The stimulated IFN-γ production is achieved according to this invention because of the presence in the cultures of an increased level of mRNA for interferon. This increased level of mRNa for IFN-γ is believed to result because of increased expression of the gene for IFN-γ and/or increased stability for IFN-γ mRNA. Because of this, the techniques described herein can be employed in the isolation of mRNA for IFN-γ, the subsequent cloning of the genetic sequence for IFN-γ, and the subsequent production of IFN-γ by recombinant DNA technology. Such a method involves: formation of a culture of IFN-γ producing cells, preferably lymphocytes; the addition of a diterpene compound to stimulate cellular elaboration of IFN-γ; optionally, the addition of an IFN-γ inducer, such as PHA; incubation of the cells under conditions conducive to IFN-γ production; extraction from the culture of RNA; purification of the RNA to produce a fraction enriched in mRNA for IFN-γ; preparation of complementary DNA for IFN-γ, employing the enzyme, reverse transcriptase, or other art-recognized techniques; incorporation of DNA for IFN-γ in a cloning vehicle, such as a bacterial plasmid; and, insertion of the DNA for IFN-γ into a microorganism.

The invention can be further specifically illustrated by the following examples.

EXAMPLE 1

Enhancement of PHA-Induced γ Interferon Production by TPA

The following procedure was employed, unless different conditions are specifically recited. Lymphocytes from freshly collected heparinized venous blood were collected as follows. Leukocyterich plasma was centrifuged on Ficoll-Hypaque gradients. Cells collected from the interface enriched for lymphocytes were employed for the seeding of cultures. Multiple-well plastic tissue culture plates were seeded with $2 \times 10^6$ mononuclear cells/ml of RPMI 1640 medium. Culture fluids were collected after different periods of incubation with the inducer 37° C. in 5% $CO_2$. Interferon titrations were done by a microassay based on inhibition of vesicular stomatitis virus in human GM-258 cells with trisomy 21. See Havell, E. A. et al., *J. Gen. Virol.* 38, 51 (1978).

By employing these general techniques, a number of plant lectins were screened for their induction capability for γ interferon employing human lymphocyte cell cultures. TPA was added at a concentration of 5 ng/ml to the lymphocyte cultures three hours prior to addition of the appropriate lectins. The results were:

| Source of Lectins | Lectin Concentration | | | |
|---|---|---|---|---|
| | 10 μg/ml | | 100 μg/ml | |
| | No TPa | TPA | No TPA | TPA |
| | Interferon, Units/ml | | | |
| *Phaseolus vulgaris* (PHA) | 560 | 15,360 | <40 | 2,560 |
| *Dolichos biflorus* (DBA) | <40 | 120 | <40 | 120 |
| *Solanum tuberosum* | <40 | 80 | <40 | 80 |
| *Sophora japonica* | <40 | 160 | <40 | 80 |
| *Maclura pomifera* | <40 | 960 | <40 | 120 |
| *Pisum sativum* | <40 | 3,840 | 40 | 5,120 |
| *Ulex europeus* (anti-HF) | <40 | 240 | <40 | 160 |
| *Ulex europeus* (anti-HC) | <40 | 120 | | N.D. |
| *Arachis hypogaea* | <40 | 120 | <40 | 80 |
| *Glycine max* | <40 | 40 | <40 | <40 |
| *Canavalia ensiformis* (ConA) | 240 | 10,240 | <40 | 960 |
| *Triticum vulgaris* (WGA) | 240 | 960 | <40 | 240 |
| *Ricinus communis* (RCA-120) | Toxic | | Toxic | |
| *Lycopersicon esculentum* | <40 | 40 | <40 | <40 |
| *Phytolacca americana* (PWM) | 1,280 | 5,120 | 960 | 5,120 |
| *Listeria monocytogenes* (LPS) | <40 | 80 | <40 | 40 |

These results illustrate that TPA was effective in enhancing γ interferon production for most of the lectins tested. Under these conditions, the enhancement of interferon production provided by the addition of TPA was several fold in most instances, and ranged up to more than 100-fold.

EXAMPLE 2

Effect of Cell Density on TPA-Enhanced PHA-Induced γ Interferon Production

Effective cell density was studied employing the procedures of Example 1 with pretreatment for 3 hours with 5 ng/ml TPA followed by the addition of 5 μg/ml phytohemagglutinin (PHA) in lymphocyte cultures maintained at 37° C. in a humidified $CO_2$ incubator for 48 hours. The results were:

| Cells × $10^6$/ml | Interferon, Units/ml |
|---|---|
| 1.0 | 2,560 |
| 1.5 | 5,120 |
| 2.0 | 7,680 |
| 2.5 | 10,240 |
| 3.0 | 10,240. |

The results indicate that interferon enhancement increased with cell density up to about $2.5 \times 10^6$ cells/ml, at which point production leveled off.

EXAMPLE 3

Effect of Pre-Treatment Time for TPA-Enhanced, PHA-Induced γ Interferon Production The effect of different times of pre-treatment was also studied employing the procedures of Example 1 and TPA at a concentration of 5 ng/ml and PHA at a concentration of 5 μg/ml. The results were:

| Hours of TPA Pre-treatment | Interferon, Units/ml |
|---|---|
| 0 | 960 |
| −1 | 1,760 |
| −2 | 1,600 |
| −3 | 1,280 |
| −4 | 1,920 |
| −5 | 1,120 |
| −16 | 960 |
| −24 | 800 |
| No TPA | 400. |

The data indicate that it is preferable to pretreat for at least 1 hour and that pre-treatment beyond 5 hours seems to result in some loss of enhancement under these conditions.

EXAMPLE 4

Effect of Incubation Time on TPA-Enhanced, PHA-Induced γ Interferon Production The effect of incubation time was studied employing the procedures of Example 1 and using cultures of human lymphocytes with 5 ng/ml of TPA added 2 hours prior to the addition of 5 μg/ml of PHA. The results were:

| Hours of Incubation | Interferon, Units/ml | |
|---|---|---|
| | No TPA | TPA |
| 48 | 200 | 2,300 |
| 60 | 280 | 5,120 |
| 72 | 800 | 15,360 |
| 96 | 1,420 | 30,720 |
| 114 | 3,200 | 35,840 |
| 144 | 1,280 | 32,000 |
| 168 | 1,280 | 30,720. |

IFN-γ production with and without TPA addition increased up to about 100 hours of incubation, after which time a levelling off in interferon yields seemed to appear.

EXAMPLE 5

Effect of PHA Concentration on TPA-Enhanced, PHA-Induced γ Interferon Production The effect of PHA concentration was studied in lymphocyte cultures employing the procedures of Example 1 without any TPA and with 5 ng/ml TPA added 3 hours prior to addition of the appropriate concentration of PHA. The results were:

| PHA, µg/ml | Interferon, Units/ml | |
|---|---|---|
| | No TPA | TPA |
| 0 | <40 | <40 |
| 1 | <40 | 3,840 |
| 2 | 400 | 3,840 |
| 4 | 560 | 7,680 |
| 6 | 800 | 7,680 |
| 8 | 280 | 7,680 |
| 10 | 240 | 5,120 |
| 15 | 320 | 4,480 |
| 20 | 320 | 3,840 |
| 35 | 100 | 3,840 |
| 50 | 40 | 1,280 |

Under these conditions, enhancement by TPA increased with increasing PHA concentration up to about 8 µg/ml, after which a decrease in enhancement was noted.

EXAMPLE 6

Effects of Varying TPA and PHA Concentrations on TPA-Enhanced, PHA-Induced γ Interferon Production The combined effects of varying TPA and PHA concentrations on the production of human IFN-γ from human lymphocyte cultures was studied employing the procedures of Example 1 and wherein TPA was added for 3 hours prior to PHA addition. The results were:

| TPA at −3 hr ng/ml | PHA, µg/ml | | | |
|---|---|---|---|---|
| | 0 | 0.5 | 5.0 | 50 |
| | Interferon, Units/ml | | | |
| 0 | <40 | 3,840 | 3,200 | 40 |
| 0.5 | <40 | 7,680 | 4,400 | 80 |
| 1.5 | <40 | 5,600 | 2,400 | 240 |
| 2.5 | <40 | 3,200 | 3,840 | 480 |
| 5.0 | <40 | 12,800 | 12,800 | 5,120 |
| 7.5 | <40 | 15,360 | 10,240 | 3,680 |
| 10 | <40 | 10,240 | 12,800 | 2,560 |
| 20 | <40 | 25,600 | 25,600 | 7,680 |
| 35 | <40 | 7,680 | 17,920 | 5,760 |
| 50 | <40 | 7,680 | 6,400 | 1,600 |

These results indicate that 5–20 ng/ml is the optimal range of TPA concentration for enhancing IFN-γ production with three different PHA concentrations under these conditions.

EXAMPLE 7

TPA-Enhancement of Mitogen-Induced γ Interferon Production

The enhancement by TPA of γ interferon production induced by various mitogens was studied employing the procedures of Example 1, except that various mitogens were substituted for the inducers of Example 1. In cultures receiving combined treatment, TPA at a concentration of 5 ng/ml was added 3 hours before the mitogen (added in concentrations listed below). The results were:

| Treatment | | IFN titer in units/ml |
|---|---|---|
| PHA | (5 µg/ml) | <40 |
| TPA/PHA | | 1,760 |
| SEA [1] | (0.02 µg/ml) | 160 |
| TPA/SEA | | 640 |
| SEA | (0.10 µg/ml) | 160 |
| TPA/SEA | | 640 |
| PHA | (5 µg/ml) | 960 |
| TPA/PHA | | 5,120 |
| Gal. Oxid. | (10 units/ml) | 320 |
| TPA/Gal. Oxid. | | 1,280 |
| PHA | (5 µg/ml) | 40 |
| TPA/PHA | | 1,280 |
| Protein A [2] | (10 µg/ml) | 250 |
| TPA/Protein A | | 800 |

[1] Purified staphlococcal enterotoxin A
[2] From *Staphylococcus aureus*

EXAMPLE 8

Enhancement of PHA-Induced IFN-γ Production by Various Phorbol Esters

The enhancement of PHA-induced IFN-γ production by various phorbol esters was studied employing the procedures of Example 1 except that the phorbol ester noted below was substituted for TPA and plateletpheresis residues ($6 \times 10^6$ cells/ml) were employed in place of fresh blood. PHA in a concentration of 5 µg/ml was added 3 hours after treatment of cell cultures with the phorbol ester. Interferon titer was done with diploid fibroblasts employing EMC virus and the results are expressed in laboratory units. The results were:

| | | INTERFERON TITER (UNITS/ML) | | | |
|---|---|---|---|---|---|
| | | Phorbol ester concentration (ng/ml) | | | |
| | | 5 | | 500 | |
| Experiment | Treatment | Without PHA | With PHA | Without PHA | With PHA |
| 1 | None | <40 | <40 | | |
| | Phorbol | <40 | <40 | <40 | <40 |
| | 4α-Phorbol | <40 | <40 | <40 | <40 |
| | P12-M13-A (TPA) | 120 | 3,840 | <40 | 4,320 |
| | 4-0-MeP12-M13-A | <40 | <40 | <40 | 1,600 |
| | P12-M13-A20-al | <40 | 110 | <40 | 2,350 |
| | P12-M | <40 | <40 | <40 | 2,560 |
| | P12,13-diD | <40 | 290 | <40 | 2,350 |
| | 4α-P12,13-diD | <40 | <40 | <40 | <40 |
| | P12,13-diB | <40 | 1,920 | <40 | 3,000 |
| | P12,13-diBz | <40 | <40 | <40 | 4,300 |
| | P12,13-diA | <40 | <40 | −240 | 3,680 |
| | P13,20-diA | <40 | <40 | <40 | <40 |
| 2 | None | <40 | 160 | | |
| | Phorbol | <40 | 160 | <40 | 160 |
| | 4α-Phorbol | <40 | 150 | <40 | 160 |
| | P12-M13-A (TPA) | <40 | 5,120 | <40 | 2,560 |

EXAMPLE 9

Comparative Enhancement by TPA and MZN on PHA-Induced IFN-γ Production

The comparative enhancement by TPA and Mezerein (MZN) on PHA-Induced IFN-γ production was studied employing the procedures of Example 8, except as noted. PHA in a concentration of 5 µg/ml was added 3 hours after treatment of cell cultures with TPA or MZN. Unprocessed plateletpheresis residues were tested, as well as mononuclear cells isolated from these residues. Interferon titer values are in laboratory units/ml of medium collected 48 hours after addition of PHA to the cultures. The results were:

|  | INTERFERON TITER | | | |
|---|---|---|---|---|
|  | Ficoll-hypaque isolated mononuclear cells | | Unprocessed platelet-residue | |
| Treatment | $2 \times 10^6$ cells/ml | $6 \times 10^6$ cells/ml | $2 \times 10^6$ cells/ml | $6 \times 10^6$ cells/ml |
| None | <40[b] | <40 | <40 | <40 |
| PHA (5 μg/ml) | 320 | 1,280 | 640 | <40 |
| TPA (5 ng/ml) | <40 | <40 | 2,560 | 10,240 |
| TPA/PHA[a] | 240 | 3,840 | 2,560 | 20,480 |
| MZN (5 ng/ml) | <40 | 160 | 5,120 | 10,240 |
| MZN/PHA | 320 | 5,120 | 15,360 | 7,680 |
| MZN (50 ng/ml) | <40 | 160 | 5,120 | 40,960 |
| MZN/PHA | 640 | 5,120 | 10,240 | 40,960 |

EXAMPLE 10

TPA-Enhancement of OKT3- and PHA-Induced IFN-γ Interferon Production and Effect of Different White Blood Cells and Cell Concentrations The effects of TPA on IFN-γ production induced with PHA or OKT3 monoclonal antibody, or without a separate inducer, were studied employing different white blood cell concentrations of both isolated monoclear cells and unprocessed plateletpheresis residues. In general, the procedures of Example 8 were employed, except as noted.

OKT3 is a monoclonal antibody against T cells. See Van Wauwe, J. P., DeMey, J. R., Goossens, J. G., "OKT3: A Monoclonal Anti-Human T Lymphocyte Antibody With Potent Mitogenic Properties," *J. Immun.* 124, 2708-13 (1980). 5 ng/ml of TPA was added to the cultures 3 hours prior to addition to 20 ng/ml of OKT3. The results were:

harvested by scraping with the aid of a rubber policeman in a phosphate-buffered saline (PBS). In a typical experiment, $4 \times 10^9$ cells were pelleted by centrifugation at $800 \times g$ for 5 min and resuspended in about 4 ml of PBS. Cells were then dispersed into 80 ml ice-cold RSB (10 mM Tris-HCl, pH 7.5, 10 mM NaCl, 1.5 mM $MgCl_2$) containing 10 mM ribonucleoside-vanadyl complexes in a 150 ml corex tube. NP-40 was added to 0.3% (v/v) and, after thorough mixing, nuclei were removed by centrifugation at 3000 rpm for 5 min in a Sorval GSA rotor. The supernatant was poured off into a corex tube which contained 4 ml of 10% $NaDodSO_4$, 4 ml of 2M Tris-HCl, pH 9.0, and 2 ml of 0.25M EDTA, and immediately extracted by phenol. The extraction was repeated twice and RNA was then precipitated by ethanol. Oligo(dT)-cellulose column chromatography was carried out according to the method of Taniguchi et al. See Taniguchi, T., Sakai, M., Fuji-Kuriyama, Y., Muramatsu, M. Kobayashi, S. and Sudo, T., *Proc. Japan Acad. Sci.* 55(B), 464-9 (1979).

Fractionation of the mRNAs by Sucrose Gradient Centrifugation

Poly(A)-containing mRNA was heated at 70° C. for 2 min and fractionated on a 5-25% linear sucrose gradient in 50 mM Tris-HCl, pH 7.5, 0.2M NaCl, and 1 mM EDTA by centrifugation at 26,000 rpm for 19 hours at 4° C. in a Hitachi PRS 40 Ti rotor. Ribosomal RNA was sedimented in a parallel tube as size marker. Twenty-one fractions were collected and RNA in each fraction was precipitated by ethanol.

Translation of IFN-γ mRNA in X. laevis oocytes

Microinjection of mRNA into *X. laevis* oocytes was carried out as described by Pang et al. See Pang, R. H. L., Hayes, T. G. and Vilcek, J. (1980) Proc. Nat. Acad. Sci. U.S.A. 77, 5341-3545. In the case of total poly(A)-RNA, RNA was dissolved in a solution of 10 mM Tris-HCl, pH 7.5, 88 mM Na Cl (oocyte injection buffer) at the concentration of 0.5 or 1 mg per ml. Groups of 10 oocytes were incubated in 0.1 ml of Barth's medium for 24 hours at 24° C. The oocytes were then homogenized

| Treatment | Ficoll-hypaque Isolated Mononuclear Cells | | | | Unprocessed Platelet-Residue | | | |
|---|---|---|---|---|---|---|---|---|
|  | $1 \times 10^6$ cells/ml | $2 \times 10^6$ cells/ml | $3 \times 10^6$ cells/ml | $6 \times 10^6$ cells/ml | $1 \times 10^6$ cells/ml | $2 \times 10^6$ cells/ml | $3 \times 10^6$ cells/ml | $6 \times 10^6$ cells/ml |
| NONE | <40 | <40 | <40 | <40 | <40 | <40 | <40 | <40 |
| TPA | <40 | <40 | <40 | <40 | <40 | 240 | 480 | 3840 |
| OKT-3 | 160 | 240 | 120 | 160 | 960 | 2560 | 2560 | 320 |
| TPA/OKT-3 | <40 | 80 | 160 | 640 | 320 | 2560 | 10240 | 10240 |
| PHA | 40 | 40 | 160 | 80 | 160 | 240 | 320 | 80 |
| TPA/PHA | 20 | 160 | 320 | 1920 | 480 | 1920 | 5120 | 5120 |

EXAMPLE 11

Preparation of Biologically Active Human IFN-γ mRNA

Production and Extraction of IFN-γmRNA

Induction of IFN-γ in human lymphocytes by PHA in the presence of TPA was carried out as described in Example 8. Briefly, mononuclear cells were isolated from lymphocyte-rich "platelet residues" by centrifugation at $400 \times g$ for 30 min on a Ficoll-hypaque gradient (Pharmacia). Cultures containing $6 \times 10^6$ mononuclear cells per ml in serum-free RPMI 1640 medium (Gibco) were treated with 5 mg/ml TPA (Consolidated Midland Corp.) for 2 hours; PHA (Burroughs Wellcome) was then added at the concentration of 5 μg/ml. After incubation for the appropriate time at 37° C., cells were and the extract was assayed for IFN activity.

Assay of IFN-γ

IFN activity was assayed by inhibition of the cytopathic effect of vesicular stomatitis virus (VSV) or encephalomyocarditis (EMC) virus in human GM-258 cells using the methods of Yip et al. See Yip, Y. K., Pang, R. H. L., Urban, C. and Vilcek, J. (1981) Proc. Nat. Acad. Sci. USA 00, 000-000. Since no reference standard for human IFN-γ was available, all results are expressed in "laboratory units."

Effect of TPA on the yield of PHA-induced IFN-γ and its mRNA

IFN yields obtained from cultures of mononuclear cells induced with PHA alone or by the combined treatment with TPA and PHA were as follows:

| Platelet | Interferon Titer | | |
|---|---|---|---|
| | One-ml Culture | | Bulk Culture |
| Residue No. | PHA | TPA/PHA | TPA/PHA |
| 1 | 80 (24) | 5,120 (24) | 5,120 (40) |
| | 120 (48) | 1,280 (48) | |
| | 40 (144) | 2,560 (144) | |
| 2 | 1,280 (72) | 1,920 (72) | 1,280 (24) |
| 3 | 1,280 (114) | 5,120 (114) | 2,560 (24) |
| 4 | 1,920 (138) | 640 (138) | 2,560 (24) |
| 5 | <40 (90) | 3,840 (90) | 2,560 (24) |
| 6 | <40 (90) | 20,480 (90) | 5,120 (24) |

The one-ml cultures were done in 24-well microplates and the bulk cultures were done in 100 to 120 ml volumes in 140 cm diameter petri dishes. The numbers in parentheses denote time of harvesting in hours after the addition of PHA. TPA was added at −2 hours.

IFN yields obtained after stimulation with PHA were quite variable, with cells from some donors producing over 1,000 units/ml, but with some other units producing much lower or undetectable amounts of IFN. In contrast, cultures induced by the combined treatment with TPA and PHA produced relatively more uniform IFN yields, due to a marked enhancement of IFN production in cells which responded poorly to induction with PHA in the absence of TPA. Culture volume did not appear to greatly affect IFN production as similar yields were obtained in 1 ml microcultures and in bulk cultures of 100 to 120 ml. The same concentration of $6 \times 10^6$ mononuclear cells per ml was employed in both types of cultures. Although the kinetics of IFN production proved to be somewhat variable, the results showed that high IFN yields were reached by 24 hours after stimulation. Therefore, in experiments aimed at the extraction of IFN-γ mRNA, cells were harvested between 16 and 36 hours after induction. Most extractions were carried out from cells harvested at 24 hours after stimulation.

To ascertain the suitability of the TPA/PHA stimulation for the extraction of IFN-γ mRNA, the following experiment was performed. Mononuclear cells (about $5 \times 10^9$ total) obtained by Ficoll-hypaque centrifugation from one donor's platelet residue were divided into two halves. One half of the cells was first incubated with 500 units/ml of human IFN-β (fibroblast IFN) for 2 hours and then stimulated with PHA (5 μg/ml). Such "priming" with human IFN-α or β has been shown to cause enhancement of PHA-stimulated IFN-γ production. See Wiranowska-Stewart, M.; Lin, L. S.; Braude, I. A. and Stewart, W. E., II; "Production, Partial Purification and Characterization of Human and Murine Interferon—Type II," *Molecular Immunology*, Vol. 17, pages 625–633 (1980). The other half of the cells was incubated for 2 hours with TPA and then stimulated with PHA. At 16 hours after the addition of PHA, cells were harvested from both groups of cultures, and mRNA was isolated by phenol extraction and oligo(dT)-cellulose column chromatography. Activity of the mRNA preparations isolated from the two groups of cultures was compared by injecting them at the same concentration into *X. laevis* oocytes and assaying oocyte extracts for interferon activity. The mRNA extracted from PHA-induced cells primed with IFN-β produced no detectable IFN activity on oocyte injection (<16 units/ml). In contrast, mRNA from TPA/PHA-induced cells produced clearly demonstrable IFN activity (maximum 196 units/ml).

On the basis of this experiment, all subsequent mRNA extractions were done from cells induced by the combined TPA/PHA treatment.

RNA was extracted from TPA/PHA-induced cells derived from seven residues (representing a total of $3.4 \times 10^{10}$ cells). Cells from each residue were cultured and extracted separately. A total of 40 mg of RNA was obtained and pooled. Of this RNA, 33 mg was processed by oligo(dT)-cellulose column chromatography. Elution of the oligo(dT)-cellulose column yielded 900 μg of RNA which could be further purified by sucrose density gradient centrifugation or other method.

Antigenic Properties of IFN produced in Oocytes

One of the important characteristics of IFN-γ is its lack of neutralization by antisera prepared against human IFN-α or IFN-β. To ascertain that IFN synthesized in oocytes injected with RNA from TPA/PHA-induced mononuclear cells is indeed IFN-γ, its affinity was examined to a serum with high neutralizing activity againsst IFN-α and β. Oocyte-derived IFN-γ was extract of *X. laevis* oocytes injected with sucrose gradient centrifugation-purified fraction of mRNA isolated from cultured mononuclear cells stimulated with TPA/PHA. Control oocyte extract was from oocytes injected with buffer. Anti-IFN (α and β) was antiserum produced by immunization of a rabbit with human IFN-α, containing neutralizing antibodies against IFN-α and IFN-β (but not IFN-γ). IFN preparations were incubated with an excess of this antiserum or with a control serum (no antibody) for 1 hour at 37° C. and then assayed for IFN activity. The results were:

| | IFN titer | |
|---|---|---|
| IFN preparation | No antibody | With anti-IFN (α + β) |
| Oocyte-derived IFN-γ | 384 | 512 |
| Oocyte-derived IFN-β | 512 | <4 |
| Control IFN-α | 1024 | <4 |
| Control IFN-β | 128 | <4 |
| Control IFN-γ | 512 | 768 |
| Control oocyte extract | <4 | <4 |

This oocyte-derived interferon preparation was not neutralized, indicating that the activity was due to neither IFN-α nor IFN-β and, therefore, it was likely to be IFN-γ. A control preparation of oocyte-derived IFN-β produced in the same batch of oocytes by injection with mRNA extracted from poly(I).poly(C)-induced human fibroblasts was neutralized by this antiserum. Control human IFN-α and IFN-β preparations (reference standards G-023-901-527 and G-023-902-527, respectively) were both completely neutralized by the antiserum while a control preparation of TPA/PHA induced INF-γ was not.

Industrial Applicability

The invention described herein is useful in the production of human IFN-γ, which in turn is useful as an antiviral agent, immunoregulatory agent, agent for affecting cell division, and anticancer drug. The enhancement gained is also useful in the production of IFN-γ by recombinant DNA techniques or other biochemical techniques employing mRNA for IFN-γ.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. In the production of human IFN-γ from IFN-γ-producing leukocyte cells:
the improvement of stimulating IFN-γ production by contacting said cells with an effective IFN-γ-production-stimulating amount of at least one IFN-γ stimulating diterpene compound and thereafter isolating IFN-γ.

2. The improvement of claim 1 wherein said diterpene compound comprises a phorbol ester.

3. The improvement of claim 2 wherein said phorbol ester comprises 12-0-tetradecanoylphorbol-13-acetate.

4. The improvement of claim 1 wherein said diterpene compound comprises mezerein.

5. A method of producing human IFN-γ, comprising:
(a) forming a cell culture of human IFN-γ-producing leukocyte cells in a suitable cell culture medium;
(b) introducing an IFN-γ inducing material into said cell culture in an effective inducing amount;
(c) introducing an IFN-γ stimulating diterpene compound into said culture in an effective IFN-γ-production-stimulating amount;
(d) maintaining said cell culture under conditions conducive to IFN-γ production; and
(e) isolating IFN-γ from said cell culture.

6. The method of claim 5 additionally including the step of introducing a human IFN-γ inducer into said cell culture in an effective IFN-γ-inducing amount.

7. A method of claim 6 wherein said IFN-γ inducer comprises a mitogen.

8. A method of claim 6 wherein said IFN-γ inducer comprises a plant lectin.

9. A method of clam 8 wherein said plant lectin comprises phytohemagglutinin.

10. A method of claim 8 wherein said patent lectin comprises concanavalin A.

11. A method of claim 6 wherein said IFN-γ inducer comprises a bacterial toxin.

12. A method of claim 11 wherein said bacterial toxin comprises staphylococcal enterotoxin A.

13. A method of claim 6 wherein said IFN-γ inducer comprises an enzyme.

14. A method of claim 13 wherein said enzyme comprises galactose oxidase.

15. A method of claim 6 wherein said IFN-γ inducer comprises Staphylococcal protein A.

16. A method of claim 6 wherein said IFN-γ inducer comprises antilymphocyte antiserum.

17. A method of claim 16 wherein said antilymphocyte antiserum comprises a monoclonal antibody.

18. A method of claim 17 wherein said monoclonal antibody comprises OKT3.

19. A method of claims 5, 8, 10 or 16 wherein said IFN-γ stimulating compound comprises 12-0-tetradecanoylphorbol-13-acetate.

20. A method of claims 5, 8, 10 or 16 wherein said IFN-γ stimulating compound comprises mezerein.

21. A method of claim 5 wherein said IFN-γ stimulating compound comprises a compound represented by the structural formula

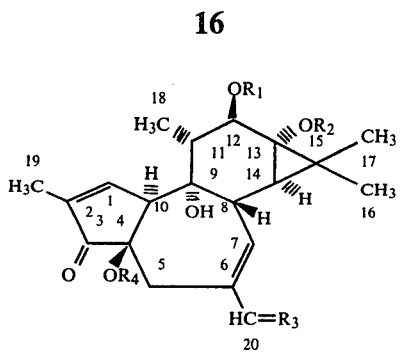

wherein $R_1$, $R_2$, $R_3$ and $R_4$ are individually selected from hydrogen, alkyl, alkoxy, carboxy, keto, aryl and alkaryl groups, and at least one of $R_1$ and $R_2$ forms an ester functionality at the 12 or 13 ring position.

22. A method of claim 21 wherein $R_1=C_{13}H_{27}CO-$, $R_2=CH_3CO-$, $R_3=H$ or $OH$, and $R_4=H$.

23. A method of claim 5 wherein said IFN-γ stimulating comprises a compound represented by the structural formula

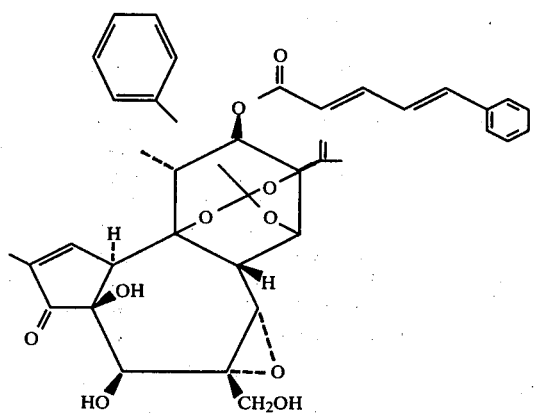

24. A method of claims 5, 21 or 23 wherein said IFN-γ producing cells comprise unprocessed cytopheresis residues or unprocessed buffy coat cells.

25. In a method for producing mRNA for IFN-γ in a culture of IFN-γ producing white blood cells including contacting said cells with an IFN-γ inducer:
the improvement of contacting said cells with an effective amount of an IFN-γ-stimulating diterpene compound to thereby raise the level of mRNA for IFN-γ in said culture and thereafter isolating said mRNA for IFN-γ.

26. A method of producing mRNA for IFN-γ, comprising:
(a) forming a culture of IFN-γ producing leukocyte cells;
(b) adding an IFN-stimulating diterpene compound to said culture in an effective amount for enhancing cellular elaboration of IFN-γ;
(c) optionally adding an IFN-γ inducer to said culture;
(d) incubating said cells under conditions conducive to IFN-γ production;
(e) extracting RNA from said culture;
(f) purifying said RNA to produce a fraction enriched in mRNA for IFN-γ.

27. A method of claim 26 wherein said diterpene compound comprises a phorbol ester.

28. A method of claim 27 wherein said phorbol ester comprises 12-0-tetradecanoylphorbol-13-acetate.

29. A method of claim 26 wherein said diterpene compound comprises mezerein.

30. A method of producing IFN-γ, comprising:
(a) forming a culture of IFN-γ-producing white blood cells;
(b) introducing an effective IFN-γ-inducing amount of an IFN-γ inducer and an effective IFN-γ-stimulating amount of mezerein into said culture;
(c) maintaining said culture under conditions conducive to the production of IFN-γ; and
(d) isolating human IFN-γ.

31. A method of producing human IFN-γ, comprising:
(a) forming a culture of IFN-γ-producing white blood cells;
(b) introducing an effective IFN-γ-inducing amount of an IFN-γ inducer and an effective IFN-γ-stimulating amount of phorbol ester into said culture;
(c) maintaining said culture under conditions conducive to the production of IFN-γ; and,
(d) isolating human IFN-γ.

32. A method of claim 31 wherein said phorbol ester comprises 12-O-tetradecanoylphorbol-13-acetate.

* * * * *